United States Patent [19]
Rogers

[11] 4,281,648
[45] Aug. 4, 1981

[54] INFLATABLE CONDOM

[76] Inventor: M. Maurice Rogers, Rte. 1, Box 214, Downsville, La. 71234

[21] Appl. No.: 78,443

[22] Filed: Sep. 24, 1979

[51] Int. Cl.³ .......................... A61F 5/00; A61F 13/00
[52] U.S. Cl. .................................. 128/79; 128/132 R
[58] Field of Search ................ 128/132, 79, 294, 295; D24/99; 46/87

[56] References Cited

U.S. PATENT DOCUMENTS

| | | | |
|---|---|---|---|
| 3,495,589 | 2/1970 | Clement | 128/79 |
| 3,820,533 | 6/1974 | Jones | 128/79 |
| 4,050,449 | 9/1977 | Castellana et al. | 128/79 X |

FOREIGN PATENT DOCUMENTS

| | | | |
|---|---|---|---|
| 672315 | 2/1939 | Fed. Rep. of Germany | 128/294 |
| 835637 | 4/1952 | Fed. Rep. of Germany | 128/79 |

*Primary Examiner*—Stephen C. Pellegrino

[57] ABSTRACT

An inflatable condom, prophylactic or prosthetic device having a conventional anterior portion and retaining ring or reinforced edge with an expandible secondary portion extending from the anterior member, and having an air duct extending inside the anterior portion in communication with the secondary portion to facilitate controlled inflation of the secondary portion responsive to manipulation of a pressure bulb.

4 Claims, 6 Drawing Figures

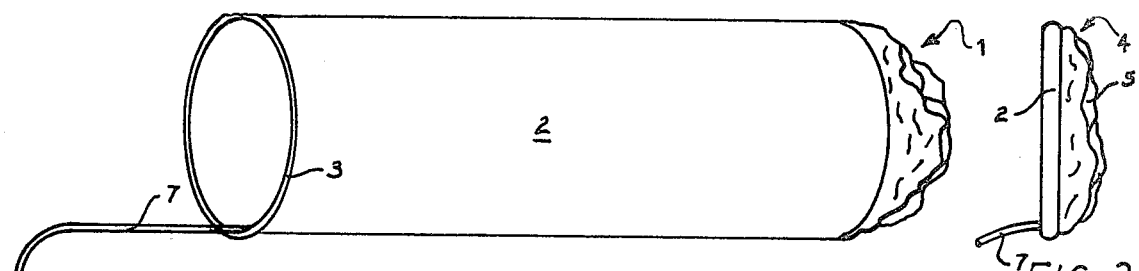
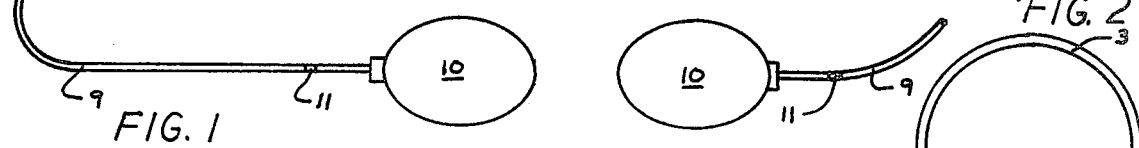
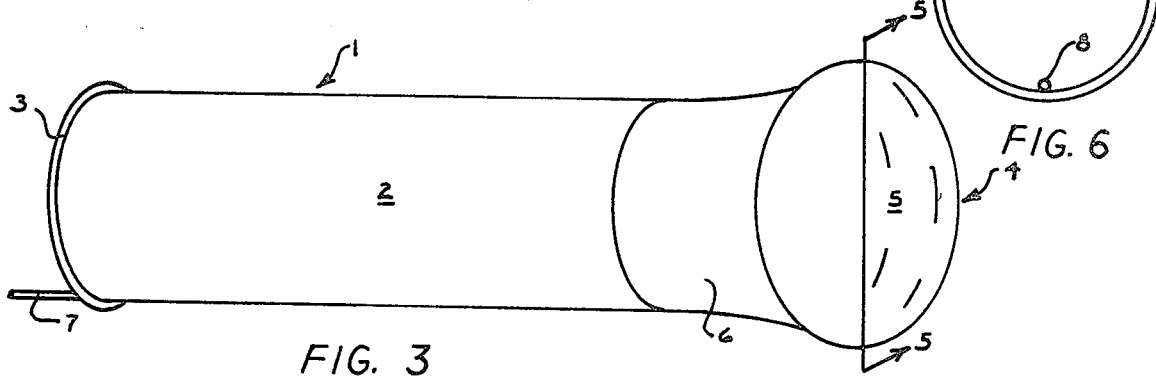
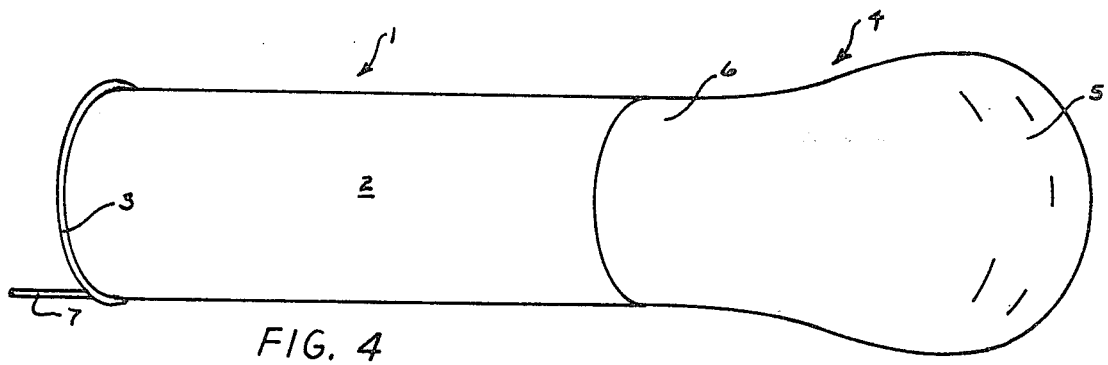
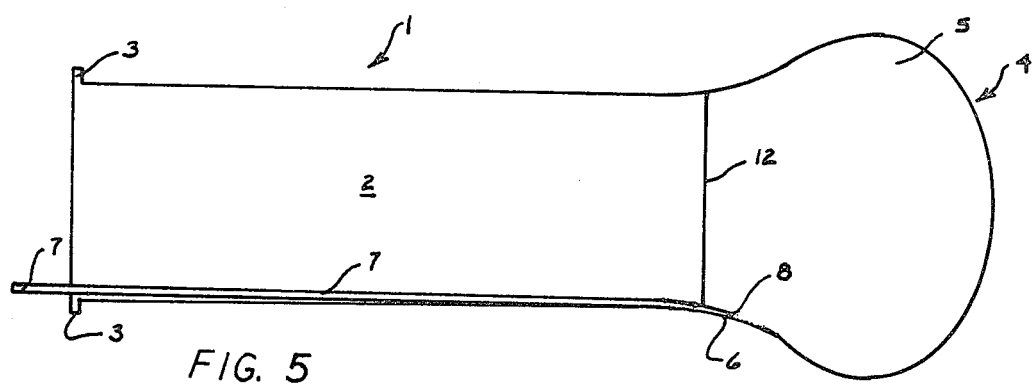

INFLATABLE CONDOM

BACKGROUND OF THE INVENTION

1. Field of the Invention

This invention relates to prophylactic and prosthetic devices, and more particularly, to a male contraceptive device or condom which is characterized by an anterior portion or sheath and an inflatable secondary portion formed integrally with the anterior portion. Controlled inflation of the secondary or balloon segment of the condom is effected by an air duct positioned inside the anterior segment and extending into the secondary portion of the condom, with air supplied through the air duct and into the secondary balloon area by means of a pressure bulb attached to the air duct utilizing tubing of suitable size, resiliency and wall thickness, such as surgical tubing. The tubing should have less elasticity than the secondary, or inflatable portion of the condom to prevent ballooning of the tubing. Controlled inflation of the secondary portion of the condom can therefore be achieved by either party during coition. Release of air pressure in the secondary portion of the condom is effected by manipulation of a pressure release valve located in the pressure bulb or in the tubing.

Contraceptives generally serve two main purposes; they ensure that conception cannot occur and they prevent the spread of disease. However, an additional important function is provided by the condom of this invention, in that the device also serves as a prosthesis to enlarge the size of the male sex organ and thus compensate for maladjustment in the two partners during coition.

2. Description of the Prior Art

Various prophylactic condoms and male prosthetic devices have been designed for various purposes in the prior art. The inflatable genital device disclosed in U.S. Pat. No. 3,495,589 to J. C. Clement is illustrative, the device being designed to ensure coition. This device includes a flexible, nonelastic sleeve designed to receive the male sex organ, with a hollow dispensible liner fitted within the sleeve and covering its inner surface, and with a means for inflating the liner and applying pressure on the organ.

It is an object of this invention to provide a new and improved inflatable condom which serves to prevent conception and the spread of disease.

Another object of the invention is to provide a new and improved, safer and more practical inflatable prosthesis which serves to enlarge the male sex organ and which can be adjusted in size during coition by either partner to achieve a desired degree of satisfaction.

Yet another object of the invention is to provide an inflatable prosthetic device which is characterized by an anterior portion or sleeve having an expandable secondary portion or sheath on the end thereof, and a duct communicating with the secondary portion with a means for selectively forcing air into the secondary portion to inflate the secondary sheath to desired proportions.

SUMMARY OF THE INVENTION

These and other objects of the invention are provided in a prophylactic or condom and prosthetic device which includes an anterior segment or portion consisting of an enlarged retaining ring or rim carrying a thin sheath, and a secondary portion or end extending the anterior sheath and expandable by controlled introduction of air into the secondary portion by means of a duct carried by the anterior segment of the condom and communicating with the secondary portion. The shape of the secondary portion can be varied by manufacturing the inflatable secondary segment or segments of the condom with a thin wall in areas where expansion is desired, and providing a thicker wall where little or no size adjustment is desired.

BRIEF DESCRIPTION OF THE DRAWINGS

A better understanding of the inflatable condom of this invention is facilitated by reference to the accompanying drawing wherein:

FIG. 1 is a perspective view of the condom with the anterior portion in extended position and the secondary portion in deflated configuration;

FIG. 2 is a side elevation of the condom illustrated in FIG. 1 in rolled configuration;

FIG. 3 is a perspective view of the condom with the secondary portion in an inflated "mushroom" configuration;

FIG. 4 is a perspective view of the condom illustrated in FIG. 1 with the secondary portion inflated in an alternative shape;

FIG. 5 is a sectional view of the condom illustrated in FIG. 3, taken along lines 5—5 in FIG. 3; and FIG. 6 is a sectional view of the condom illustrated in FIG. 1, taken along lines 6—6 of FIG. 1.

DESCRIPTION OF THE PREFERRED EMBODIMENTS

Referring now to FIGS. 1 and 2 of the drawing, the inflatable condom of this invention is generally illustrated by reference numeral 1, and is illustrated in rolled configuration in FIG. 2, with the anterior portion or sheath 2 rolled or wrapped continuously over rim 3. The secondary portion or balloon is generally illustrated by reference numeral 4, and is integrally formed with anterior portion or sheath 2, according to processes known to those skilled in the art. Secondary portion 4 is further characterized by a sheath neck 6, connecting it to anterior portion 2, and expandable sheath 5, as hereinafter described. A duct 7 is fitted to the inflatable condom 1 at or near the juncture of anterior portion 2 and secondary portion 4, which juncture is characterized by a general thickening of the condom sheath at sheath neck 6, as illustrated in FIGS. 3–5 of the drawing. The free end of duct 7 extends inside anterior portion 2 and communicates with a length of flexible tubing 9, carrying a pressure bulb 10. Inflatable condom 1 is unrolled on rim 3 to the configuration illustrated in FIG. 1 when it is ready for use.

Referring now to FIGS. 3, 5 and 6 of the drawing, the inflatable condom 1 is shown with expandable sheath 5 inflated in a mushroom configuration which is shaped by constructing sheath neck 6 slightly thicker than expandable sheath 5 during manufacture of the condom, thereby inhibiting inflation of the sheath neck. Inflation of expandable sheath 5 is achieved by initially pumping pressure bulb 10 to force air through tubing 9 and into duct 7, and from duct mouth 8 of duct 7, into secondary portion 4, as illustrated in FIGS. 5 and 6. The duct 7 is sealed in inner wall 12 of secondary portion 4, with inner wall 12 forming an air-tight seal between anterior portion 2 and secondary portion 4, permitting inflation of expandable sheath 5 to the desired proportions, as illustrated in FIG. 5.

Referring now to FIG. 4 of the drawing, an alternative preferred configuration of secondary portion 4 of inflatable condom 1 is illustrated, with sheath neck or cuff 6 again performing the function of shaping expandible sheath 5. It will be appreciated by those skilled in the art that the inflated shape of secondary portion or balloon 4 can be easily selected by controlling the extent, location, elasticity and thickness of sheath neck 6 during manufacture of the condom. It will be further appreciated that the inflatable condom 1 can be manufactured of substantially any known soft and yielding elastic material according to the knowledge of those skilled in the art.

Referring again to FIGS. 1 and 2 of the drawing the size of expandible sheath 5 can be easily and safely controlled by either partner during coition by alternate manipulation of pressure bulb 10 and air valve 11, located in tubing 9, as illustrated in FIG. 2. A suitable air valve can also be provided in pressure bulb 10, as desired, it being only necessary and desirable to provide a positive and safe means for controlling the inflation of expandible sheath 5, both as to introduction and release of air pressure in the sheath. In a preferred embodiment of the invention air valve 11 is located in tubing 9 and acts as a check valve when bulb 10 is manipulated, with reverse flow of air achieved by pressing air valve 11 when it is desired to deflate expandible sheath 5.

Referring again to FIG. 5 of the drawing, in a preferred embodiment of the invention duct 7 is positioned loosely inside anterior portion 2 of inflatable condom 1 and is attached to the inside wall of sheath neck 6 with duct mouth 8 extending through inner wall 12 and into expandible sheath 5 to ensure that air will selectively flow through duct 7 and inflate expandible sheath 5. This attachment of duct 7 to sheath neck 6 permits rolling of anterior portion 2 on rim 3 to the point of attachment of duct 7, as illustrated in FIG. 2. In a preferred embodiment of the invention inner wall 12 is slightly thicker than expandible sheath 5 to facilitate minimum ballooning of inner wall 12 when expandible sheath 5 is inflated.

The inflatable condom of this invention is characterized by a high degree of safety and control, in that either party can control the extent of inflation of secondary portion 4. Furthermore, the condom can be provided in both lubricated and non-lubricated design. However, in a preferred embodiment of the invention the inflatable condom is provided with a lubricated secondary portion 4. Furthermore, as in the case of conventional condoms, both the anterior portion 2 and the secondary portion 4 can be provided with beads or ridges projecting from the surface of the sheath for greater stimulation, as desired. As in the case of conventional condoms, the inflatable condom of this invention remains in place by the pressure of anterior portion 2, and can be manufactured of a thin, highly elastic material which permits maximum sensitivity and closely controlled inflation of the secondary portion.

It will be further appreciated that the inflatable condom of this invention acts as a highly satisfactory prosthesis for increasing the size of the male sex organ to compensate for insufficient adaptation or development of the organ, surgery or injury, and organ conditions in both partners, to ensure that the female partner is completely satisfied, while providing maximum sensitivity for the male. The variation in size and shape of secondary portion 4 of inflatable condom 1 permits infinite adjustment in the condom manufacture as described above, in order to compensate for substantially any condition existing in both the male and female partner.

Having described my invention with the particularity set forth above, what is claimed is:

1. An inflatable condom comprising:
   (a) an anterior portion characterized by a generally tubular sheath open at one end and having a reinforcing rim adjacent said one end;
   (b) a secondary portion integrally formed in said anterior portion to close said anterior portion at the end opposite said one end and characterized by an expandible sheath having a relatively thin wall thickness, a sheath neck communicating between said anterior portion and said expandible sheath and an inner wall closing said sheath neck to seal said expandible sheath from said anterior portion, said sheath neck and said inner wall are thicker than said expandible sheath to facilitate minimum expansion of said sheath neck and said inner wall when said sheath is inflated;
   (c) duct means positioned inside said anterior portion and attached to said sheath neck and extending through said inner wall for inflating said expandible sheath; and pump means cooperating with said duct means for selectively inflating said expandible sheath from a point remotely located from said inflatable condom.

2. The inflatable condom of claim 1 further comprising valve means in cooperation with said duct means for selectively releasing air pressure in said expandible sheath and causing said expandible sheath to deflate.

3. The inflatable condom of claim 1 wherein said expandible sheath is shaped generally in the shape of a mushroom when in inflated configuration.

4. The inflatable condom of claim 1 wherein said pump means is a rubber bulb having air intake means and check valve means, and tubing communicating between said rubber bulb and said duct means, and said valve means is a pressure release valve positioned in said tubing.

* * * * *